US 6,589,180 B2

(12) United States Patent
Erikson et al.

(10) Patent No.: US 6,589,180 B2
(45) Date of Patent: Jul. 8, 2003

(54) ACOUSTICAL ARRAY WITH MULTILAYER SUBSTRATE INTEGRATED CIRCUITS

(75) Inventors: Kenneth R. Erikson, Henniker, NH (US); John Marciniec, Framingham, MA (US); Timothy E. White, Acton, MA (US)

(73) Assignee: Bae Systems Information and Electronic Systems Integration, INC, Nashua, NH (US)

( * ) Notice: Subject to any disclaimer, the term of this patent is extended or adjusted under 35 U.S.C. 154(b) by 0 days.

(21) Appl. No.: 10/094,851

(22) Filed: Mar. 8, 2002

(65) Prior Publication Data

US 2003/0013969 A1 Jan. 16, 2003

Related U.S. Application Data

(63) Continuation-in-part of application No. 09/969,438, filed on Oct. 2, 2001, now Pat. No. 6,524,254.
(60) Provisional application No. 60/299,634, filed on Jun. 20, 2001.

(51) Int. Cl.[7] ................................................. A61B 8/14
(52) U.S. Cl. ........................ 600/459; 310/334; 29/25.35
(58) Field of Search ................................. 600/407–471; 367/7, 11, 130, 138; 310/334; 29/25.35; 73/625, 626

(56) References Cited

U.S. PATENT DOCUMENTS

| | | | |
|---|---|---|---|
| 5,311,095 A | | 5/1994 | Smith et al. |
| 5,548,564 A | | 8/1996 | Smith |
| 5,617,865 A | | 4/1997 | Palczewska et al. |
| 5,629,578 A | | 5/1997 | Winzer et al. |
| 5,644,085 A | | 7/1997 | Lorraine et al. |
| 5,732,706 A | * | 3/1998 | White et al. ................. 600/437 |
| 5,744,898 A | | 4/1998 | Smith et al. |
| 5,786,597 A | | 7/1998 | Lingren et al. |
| 5,834,880 A | | 11/1998 | Venkataramani et al. |
| 5,906,580 A | * | 5/1999 | Kline-Schoder et al. .... 600/459 |
| 6,087,762 A | * | 7/2000 | Corbett, III et al. ........ 310/334 |
| 6,246,158 B1 | | 6/2001 | Ladabaum |
| 6,263,551 B1 | | 7/2001 | Lorraine et al. |
| 6,409,667 B1 | * | 6/2002 | Hossack ..................... 600/443 |

OTHER PUBLICATIONS

PCT International Search Report dated Feb. 7, 2003 of International Application No. PCT/US02/07596 filed Mar. 8, 2002.

B.T. Khuri–Yakub, C.H. Cheng, F.L. Degertekin, S. Ergun, S. Hansen, X.C. Jin, O. Oralkan, Silcon Micromachined Ultrasonic Transducers, Fifth European Conference on Underwater Acoustics, Lyone France, Jul. 10–13, 2000, pp. 1367–1372.

H.T. Soh, C.P. Yue, A. McCarthy, et al. UltraLlow Resistance, Through–Wafer Via (TWV) Technology and Its Application in Three Dimensional Structures on Silicon, Japanese Journal of Applied Physics, Apr. 1999, pp. 2393–2396, vol. 38, Part I, No. 4B.

(List continued on next page.)

Primary Examiner—Marvin M. Lateef
Assistant Examiner—Ali M. Imam
(74) Attorney, Agent, or Firm—Maine & Asmus

(57) ABSTRACT

A high density, exceptionally complex and compact ultrasound transducer array using multi-layer structures composed of active integrated circuit devices on various substrates and passive devices. Electrically conducting interconnections between substrates are implemented with micro-vias configured with conductors extending through the substrates, permitting the use of divided or different integrated circuit technologies arranged and/or isolated within different integrated circuit substrates or layers of the ultrasound transducer assembly. The various layers may be assembled with solders of respectively lower reflow temperatures, to permit testing of selected layers and circuits prior to completion.

33 Claims, 10 Drawing Sheets

OTHER PUBLICATIONS

T.R. Anthony, Forming Electrical Interconnections Through Semiconductor Wafers, Journal of Applied Physics, Aug. 1981, pp. 5340–4349Vo.l. 52, No. 8.

S. Calmes, C.H. Cheng, F.L. Degertekin, X.C. Jin, B.T. Kuri–Yakub, Highly Integrated 2–D Capactive Micromachined Ultrasound Transducers, 1999 IEEE International Ultrasonics Symposium, Lake Tahoe, Nevada, Oct. 17–20, 1999, pp. 1163–1166.

X.C. Jin, C.H. Cheng, O. Oralkan, S. Calmes, F.L. Degertekin, B.T. Khuri–Yakub, Recent Progress in Capative Micromachined Ultrasonic Immersion Transducer Array, $8^{th}$ International Symposium on Integrated Circuits, Devices and Systems, ISIC–99 Proceedings, Sep. 8–10, 1999, pp. 159–162, Singapore.

E.M. Chow, A. Partridge, C.F. Quate, T.W. Kenny, Through-Wafer Electrical Interconnects Compatible with Stanford Semiconductor Processing, Solid–State Sensor and Actuator Workshop, Jun. 4–8, 2000, pp. 343–346, Hilton Head Island, SC.

C.H. Cheng, E.M. Chow, X. Jin, S. Ergun, B.T. Khuri–Yakub, An Efficient Electrical Addressing Method Using Through–Wafer VIAS for Two–Dimensional Ultrasonic Arrays, IEEE Ultrasonics Symposium, 2000, pp. 1179–1182,.

* cited by examiner-

ACOUSTICAL ARRAY WITH MULTILAYER SUBSTRATE INTEGRATED CIRCUITS

This application relates and claims priority to pending U.S. application No. 60/299,634, filed Jun. 20, 2001, and is a continuation in part to pending U.S. application No. 09/969,438, filed Oct. 2, 2001 now U.S. Pat. No. 6,524,254.

FIELD OF INVENTION

This invention relates to methods for constructing high density, exceptionally complex and compact ultrasound arrays using interconnected, multi-layer structures composed of active integrated circuit devices on various planar substrates and passive devices, and more particularly, to using electrically conducting micro-bump interconnections between layers, and conductors within micro-vias for electrical connections through the semiconductor or other substrates, to realize the implementation in a single device of segregated sections or different integrated circuit technologies on a layer-by-layer basis.

BACKGROUND

Diagnostic ultrasound is an established and growing medical imaging modality. Currently one-dimensional arrays with up to 128 elements are the standard in the industry. Separate coaxial cables are used to connect the elements to the system electronics. Improved image quality requires the use of matrix (n×m) arrays with a thousand or more elements. As element numbers increase and their dimensions grow smaller, limitations to present fabrication technologies arise. Cost, ergonomics, produce-ability and reliability are important issues. Signal loss due to the capacitance of the coax cables becomes a fundamental problem.

Connecting an integrated circuit directly to the array elements alleviates all these problems. Each unit cell of such a custom Transmitter/Receiver Integrated Circuit (TRIC) may have high voltage switches for transmitting; a preamplifier which minimizes signal loss and a multiplexer to send the array signals over fewer wires. Additional signal processing and beam forming may also be included.

This disclosure first discusses the history and current state-of-the art in medical diagnostic ultrasound, emphasizing arrays, their limitations and issues.

Diagnostic ultrasound is an established, cost-effective medical imaging modality. More than 400,000 systems are in use throughout the world. This stage of development has been achieved over the last 30 years for several reasons. The equipment and exam costs are lower than competing medical imaging technologies. Structural information about normal organs and soft tissue (non-bone) and pathologies is easily obtained. Functional information such as blood flow, organ perfusion or movement of heart valves is easily obtained. The systems are portable and only require a typical examining room. Finally, it is generally considered to be non-invasive.

Medical ultrasound systems transmit a short pulse of ultrasound and receive echoes from structures within the body. The handheld probes are most often applied to the skin using a coupling gel. Specialty probes are available for endocavity, endoluminal and intraoperative scanning.

Almost all systems on the market today produce real-time, grayscale, B-scan images. Many systems include colorflow imaging. Real-time images move as the operator moves the probe (or scanhead). Moving structures, such as the heart or a fetus, are shown on the video monitor. Grayscale images depict the strength of echo signals from the body as shades of gray. Stronger signals generally are shown as bright white. Lower signals become gray and echo-free regions are black. B-scans are cross-sectional or slice images. Colorflow imaging adds a color overlay to the black and white image to depict blood flow.

Over the last 30 years, the major technical developments that have improved imaging or added diagnostic capability. Digital technology provided image stability and improved signal processing. Real-time imaging provided quicker, easier imaging and functional information. Electronically scanned linear arrays, including sequenced arrays and phased arrays, provided improved reliability. Color-flow imaging opened up new cardiac and vascular applications. Digital beamformers improved image quality. Harmonic imaging provided improved image quality particularly in difficult to image patients. Coded-excitation imaging permitted increased penetration allowing use of higher frequency ultrasound, thereby improving image contrast. Contrast agents offer improved functional information and better image quality. And 3D (volumetric) imaging presents more easily interpreted images of surfaces such as the fetal face.

One-dimensional (1D, linear or 1×m) transducer arrays, either flat or curved, having as many as 128 transducers, are the conventional electronically scanned arrays in widespread use today. Matrix arrays consisting of (n×m) elements will be required in future systems to improve image quality. All such arrays on the market today are connected to the system electronics through a bundle of coaxial cables. Beamformers in the system electronics adjust the time delays between channels to provide electronic sector scanning and focusing. High performance systems typically use all 128 elements in their beamformers. Lower performance systems may use as few as 16 of the 128 elements at any instant. The scanning function is performed by switching elements into the aperture on the leading edge of the scan and switching out elements at the trailing edge.

When a pulse is transmitted by an array, transmitter time delays on each channel are adjusted to provide a focusing effect. For reception of echoes, time delays between channels are adjusted in real-time as the pulse propagates into the body. This dynamic, or tracking focus, sweeps out from the probe into the body at the velocity of sound. Almost all ultrasound systems use dynamic focusing, which provides greatly improved resolution and image quality in the scanning plane.

1.25D arrays typically use a (128×3) or (128×5) matrix. They are connected to the system electronics through a similar bundle of coax cables as the 1D array. The same beamformers are also used for scanning and dynamic focusing. As the pulse propagates into the body, only the center element is initially selected for receiving the reflected signals. By switching in additional elements as the pulse propagates, the receiving aperture is enlarged and the receiver is weakly focused.

1.5D arrays use a (128×n) matrix, with n an odd number, typically 5, 7 or 9.1.5D arrays use dynamic focusing in the plane perpendicular to the scanning plane. This produces optimal resolution in all dimensions, further reducing artifacts. The key difference between the 1.25D and 1.5D arrays is the active time-delay beamforming in both dimensions. The number of elements in the elevation direction is often an odd number because elements on each side of the beam axis are electrically connected together since they both have the same time delay for on-axis targets.

1.75D arrays are very similar to 1.5D arrays with the exception that the elements in the elevation direction are individually connected to the beamformer. Limited angular beamsteering can be performed in addition to dynamic focusing. Aberration correction is also possible with the 1.75D array. These added capabilities are not present in a 1.5D array, which only provides improved focusing for on-axis targets.

2D transducer arrays are the most general type, with (n×m) elements. Dynamic focusing as well as sector beamsteering in any arbitrary direction around the axis normal to plane of the array is possible. The angles are only limited by the constraints of the beam former, the number of elements and their dimensions.

The use of larger multi-dimensional arrays introduces problems of circuit density in the supporting substrate, to a much greater extent than the linear arrays currently in use. Although the 1.25D array produces moderate improvement, the improved image quality of 1.5D and 1.75D arrays will make a quantum jump in resolution, image quality and freedom from artifacts, which suggests that resolution of the circuit density problems is very important.

All linear arrays currently on the market use piezoelectric materials as the transducing mechanism from electrical signals to ultrasound (transmitter) and ultrasound back to electrical signals (receiver). The signals are generally in the form of short pulses or tone bursts. Most high performance arrays use a piezocomposite material (FIG. 6), which is fabricated by a "dice and fill" technique. The piezocomposite array structure 9 provides improved bandwidth and efficiency as well as reduced crosstalk or interference between adjacent elements. Pieces of native ceramic such as Type 3203HD made by Motorola or PZT-5H made by Morgan-Matroc are diamond sawed into pillars 18. The spaces between the pillars are filled with a polymer 28 such as DER332 epoxy made by Dow Chemical. The spaces between elements 24 are often left air-filled or are filled with a sound-absorbing polymer. Top electrode 30 is the common electrical connection between elements. Bottom electrodes 22 are delineated for each array element and are used as the electrical connections to the piezocomposite material.

In a beamsteered array, the element dimensions must be about a wavelength in the steering dimension. For example, in a 3.5 MHz (1×128) array the element width is about 0.2 mm for a total array length of approximately 64 mm. In the other dimension, the element dimensions are a tradeoff between resolution and depth of focus. For a 3.5 MHz array, this dimension is 12 to 15 mm. As the frequency of the array increases, element size decreases, as does element thickness, however, the aspect ratio remains constant. Other methods of fabrication such as laser milling or scribing, etching or deposition are under development. At present, they are not well accepted.

Behind the flex circuit is a "backing" 23 (FIGS. 5 & 7) that provides mechanical support and acoustical attenuation. When a piezoelectric transducer is electrically pulsed, two acoustical pulses 25 and 27 are generated that travel in opposite directions. Pulse 27 traveling out of the scanhead is desired, while pulse 25, propagating into the backing, is unwanted and is absorbed by the backing.

One or more "matching" layers 26 are next in the path of pulse 27. They serve to improve the coupling of energy from the piezocomposite into the body by matching the higher acoustical impedance piezocomposite to the lower acoustical impedance of the body. This matching layer functions in the same way as the anti-reflection coating on an optical lens. The system electronics "focus" the pulse in the scanning plane 34 (the "in-plane") dimension.

A simple convex lens 31 forms the front surface that contacts the patient's skin. It provides a fixed focus 33 to the sound pulse in plane 35 (the "out-of plane" dimension), which is perpendicular to scanning plane 34.

Modern systems impose increasingly stringent requirements on arrays. Some of the important parameters that characterize typical medical ultrasound arrays include the following.

Center frequency: 3.5 MHz to 10 MHz for applications in the abdomen. The trend is towards higher frequencies to improve tissue contrast and image quality. In beamsteered arrays, the elements must be about ½ wavelength wide to avoid grating lobes. This results in fabrication issues with the higher frequency arrays.

Transmitter pressure output: measured as dB re 1 microPascal/Volt. Higher output for a given drive voltage is desirable.

Receiver pressure sensitivity: measured as dB re 1 microvolt/Pa. Higher receiver sensitivity is desirable.

Insertion loss: transmitter and receiver parameters are often combined into an insertion loss value in a lossless medium, i.e. (volts output)/(volts input) expressed in dB.

Fractional Bandwidth: 50% to 120% of the center frequency. Applications such as harmonic imaging demand the widest possible bandwidth consistent with maximum transmitter output and receiver sensitivity. In a B-scan image, the resolution along the direction of the pulse is a function of bandwidth. Higher bandwidth equals shorter pulses and better resolution.

Crosstalk: Crosstalk is the interference of signals between array elements. The interference may be electrical, mechanical or acoustical. It is expressed in dB re nearest neighbor. Crosstalk in a well-constructed array better than −30 dB.

Resolution (beam pattern): The spatial resolution of the probe in the plane normal to the beam is fundamentally a function of the ultrasound wavelength and active aperture dimension. Other factors in the system electronics, including the probe bandwidth interact with this in a complex way.

Temperature Rise: For probes that contact the human body, temperature rise is an important safety issue. Probe heating is due to internal losses in the piezoelectric materials. The maximum allowable temperature rise is 5 degrees C.

Cable parameters: As the number of wires increases, retaining cable flexibility and low weight become important to minimize operator fatigue. In addition, cable capacitance, which is about 50 pF/meter (16 pF/ft) becomes important as the element size decreases with higher frequency probes. Signal losses of over 90% are not uncommon.

Scanhead size and weight: The probe must fit a small hand comfortably for extended scanning and the weight must be a minimum to reduce operator fatigue.

Reliability: The Mean-Time-Between-Failure (MTBF) must be two years or more.

As the number of elements increases and their size decreases, however, the existing approaches may no longer be feasible or practical. Processing time, touch labor, yield, reliability and cost become limiting issues and new processes are required. With higher ultrasound frequencies and more complex matrix arrays, element size decreases. The capacitance of an element decreases linearly with the area of the element. The supporting integrated circuitry in the underlying substrate contains transmitter and receiver electronics and switching circuitry, and provides an impedance translation between the small capacitance array transducers and the higher capacitance wires in the cable.

In FIG. 9, a cross-section of a prior art piezocomposite integrated array, the array elements 18 are electrically and mechanically connected to integrated circuit (IC) substrate 32 with electrically conductive bumps 34 using metallized pads 36 on IC 32 to form a complete electrical circuit. Integrated circuit substrate 32 is typically composed of silicon, although other semiconductors may be used. Conductive bumps 34 may be composed of solder or a conductive polymer such as silver epoxy.

In addition to the impedance translating electronics, signal-processing electronics may be included in the probe to greatly simplify the fabrication of all types of matrix arrays. This has the benefit of dramatically reducing the number of wires required in the cable, but adds yet further complexity and density to the supporting integrated circuitry.

The first matrix array with an integrated circuit was developed in the early 1970's. An 8×8 element 3.5 MHz receiver array with a preamplifier integrated circuit bump-bonded directly behind each 1 mm×1 mm Lithium Niobate single crystal piezoelectric element was constructed. Individual elements could be connected along a row to one of the eight output lines. Although the state of microelectronics was primitive by current standards, the array was shown to have acceptable sensitivity and demonstrated the feasibility of the approach. At that time, the diagnostic ultrasound industry was in its infancy and there was no need for such an array.

In a recent government-funded program, a real-time 3D ultrasound camera intended for Army medics to use on the front lines was designed and feasibility was proven. In this camera, an acoustical lens was used to image a volume onto a 128×128 (16,384 element) 5 MHz matrix array.

Each element of the piezocomposite array had a custom integrated circuit bump-bonded directly behind it using micro-solder balls. The piezocomposite array was air-backed, i.e. there was a small air space between the array and the IC. The bump bonds were the only mechanical and electrical connections between the array and the IC.

Each unit cell of the ROIC contained a preamplifier, signal processing, a limited amount of sampled data storage and multiplexing. The silicon was two side-buttable, permitting tiling of four pieces into the square 128×128 array. In this program, the concept of bump-bonding a matrix array directly to an integrated circuit was revalidated. Important parts of this technology are now protected by U.S. and foreign patent(s).

In another government-funded program, a camera for Navy divers to image mines in murky water was developed. The camera uses an acoustical lens as well as a second-generation 128×128 3 MHz Integrated Matrix Array. The following improvements in this new device are directly relevant to the medical ultrasound arrays. A custom Transmit and Receive Integrated Circuit (TRIC) was developed. This is the first such IC that has ever been built for an ultrasound system. The key improvement is the introduction of a 90 volt switch, enabling transmission of ultrasound pulses. The 32×64 cell IC is three-side buttable, i.e. all external connections are on one narrow edge of the silicon. This permits tiling of eight pieces of silicon to form the 128×128 array with its monolithic layer of supporting circuitry.

Moving away from the specific field of acoustical and ultrasound technologies, multi-layer printed circuit boards (PCB) have been used for many years in the electronics industry. They enable complex interconnection of multiple integrated circuits in individual packages, passive devices, connectors, etc. A conventional integrated circuit package, however, contains a silicon integrated circuit chip or die, which is wire bonded to leads that exit the package and are in turn connected to the PCB. The wire bonding together with the package require extra space as well as labor and/or further processing.

Hybrid circuit technology removes the package and wirebonds the chip directly to a passive substrate. This is very effective in miniaturizing the final assembly. However, wire bonding is still required.

The next level of complexity (or integration) is flip-chip bonding of the die directly to a passive substrate. This achieves very close to maximum chip density in a planar structure.

Recently, a further level of integration has been achieved, for example, by Irvine Sensors. Multiple layers of silicon die are sandwiched together and interconnected at the ends. This allows very high densities. There are still limitations on the circuits that may be achieved, since the interconnections are only made at the sides of the chips.

Vertical wafer feedthroughs or conductor-carrying vias for connecting an array of sensors or actuators from the transducer side to the backside of a transducer chip has been disclosed in some recent publications, as in an article entitled *An Efficient Electrical Addressing Method Using Through-Wafer Vias For Two-Dimensional Ultrasonic Arrays*, by Ching H. Cheng et al, of Stanford University, 2000 IEEE Ultrasonics Symposium-1179.

However, the particular ways, advantages and benefits of dividing and redistributing the traditional two dimensional topography of the supporting integrated circuitry of a small element, large scale two dimensional transducer array into segregated layers or substrates has not been heretofore explored.

SUMMARY OF THE INVENTION

The invention encompasses a new method for constructing ultra-high density, exceptionally complex and compact ultrasound arrays using multi-layer structures composed of active integrated circuit devices on various substrates and passive devices, using electrically conducting micro-bump interconnections between the substrates and micro-vias configured with electrical conductors through the substrates. This methodology allows the use of divided or different integrated circuit technologies on a layer-by-layer basis.

To this end there is provided a multilayer acoustical transducer array assembly for an ultrasound system consisting of an acoustical transducer array with a back side and back side pattern of electrical contacts. There is a first IC substrate with associated integrated circuitry for operating the array, where the first IC substrate has a first side with matching electrical contacts for contacting the transducer array for supporting electrical functions and a second side with second side electrical circuit contacts. The transducer array is aligned in a co-planar configuration with the first IC substrate, with the electrical contacts of the transducer array being electrically bonded to respective electrical contacts on the first side of the first IC substrate.

There is a final IC substrate with additional associated integrated circuitry for operating the array. The final IC substrate has a first side with matching electrical contacts and a second side. The IC substrates are aligned in a co-planar configuration, and the second side electrical contacts of each IC substrate are electrically bonded to respective matching electrical contacts on each adjacent IC substrate. Suitable connections to a power source may be provided by edge connections from one or more substrates, as is well known in the trade.

There may be at least one intermediate IC substrate with further associated integrated circuitry for operating the array, where the intermediate IC substrate has a first side with matching electrical contacts and a second side with second side electrical contacts. There may be an acoustical backing layer adhered to the second side of the final IC substrate.

The first IC substrate may have electrical paths connecting at least selected electrical contacts on its first side to respective selected electrical contacts on its second side. The electrical paths may consist of vias extending through the IC substrate, and the vias may have or be filled with electrically conductive materials.

The first IC substrate may further consist of integrated circuitry for selecting between groups of transducers within the transducer array. The groups of transducers may be orthogonally oriented lines of transducers within the transducer array.

The electrical contacts on any of the IC substrates may be configured as solder bumps, where the first side contacts of each substrate have higher reflow melting temperature than the second side contacts.

There is provided a multilayer acoustical transducer array assembly with at least one high density intermediate IC substrate with image processing capability for processing signals from the array. It may also be connected to a local or remote host computer and/or display. It has electrical connections with the associated integrated circuitry in the other IC substrates, which may include surface contacts and/or edge connections. There may be included in the assembly an integral planar display array, preferably aligned in a co-planar configuration with and electrically connected to the high density intermediate IC substrate. The intermediate IC substrate may have electrical paths connecting at least selected electrical contacts on its first side to respective selected electrical contacts on its second side, similar to other IC substrates of the assembly.

The integrated circuitry supporting the operation of the array may be divided between two or more substrates. The integrated circuitry in the first IC substrate may have at least switching circuitry for switching the transducers of the array between transmit and receive modes of operation. The integrated circuitry in the final IC substrate may have at least receiving circuitry for receiving signals from the array. Alternatively, the integrated circuitry in an intermediate IC substrate may have at least the switching circuitry for switching the array between transmit and receive modes of operation, or the receiving circuitry for receiving signals from the transducers of the array.

There is also provided a method for making a multilayer acoustical transducer array assembly including the steps of providing an acoustical transducer array with a back side and back side pattern of electrical contacts, a first IC substrate as described above, and a similar second IC substrate, then electrically bonding the matching electrical contacts on the first side of the first IC substrate to the electrical contacts of the array at a suitable pressure and a first temperature, and then electrically bonding the matching electrical contacts on the first side of the second IC substrate to the electrical contacts on the second side of the first IC substrate at a suitable pressure and second temperature, where the second temperature is lower than first temperature. This lower temperature sequence permits testing at least selected electrical functions of the first IC substrate at least in part through access to the electrical contacts on the second side of the first IC substrate before the assembly is completed.

The method may be extended to providing a third, similar IC substrate with additional integrated circuitry for supporting the operation of the array, and then electrically bonding the matching electrical contacts on the first side of the third IC substrate to the electrical contacts on the second side of the second IC substrate at a suitable pressure and third temperature, where the third temperature is lower than said second temperature. This lower temperature sequence provides for testing at least selected electrical functions of the second IC substrate at least in part through access to the electrical contacts on the second side of the second IC substrate before the assembly is completed.

Various embodiments are illustrated and described below, illustrative but not exhaustive of the scope of the invention.

Figure 1:
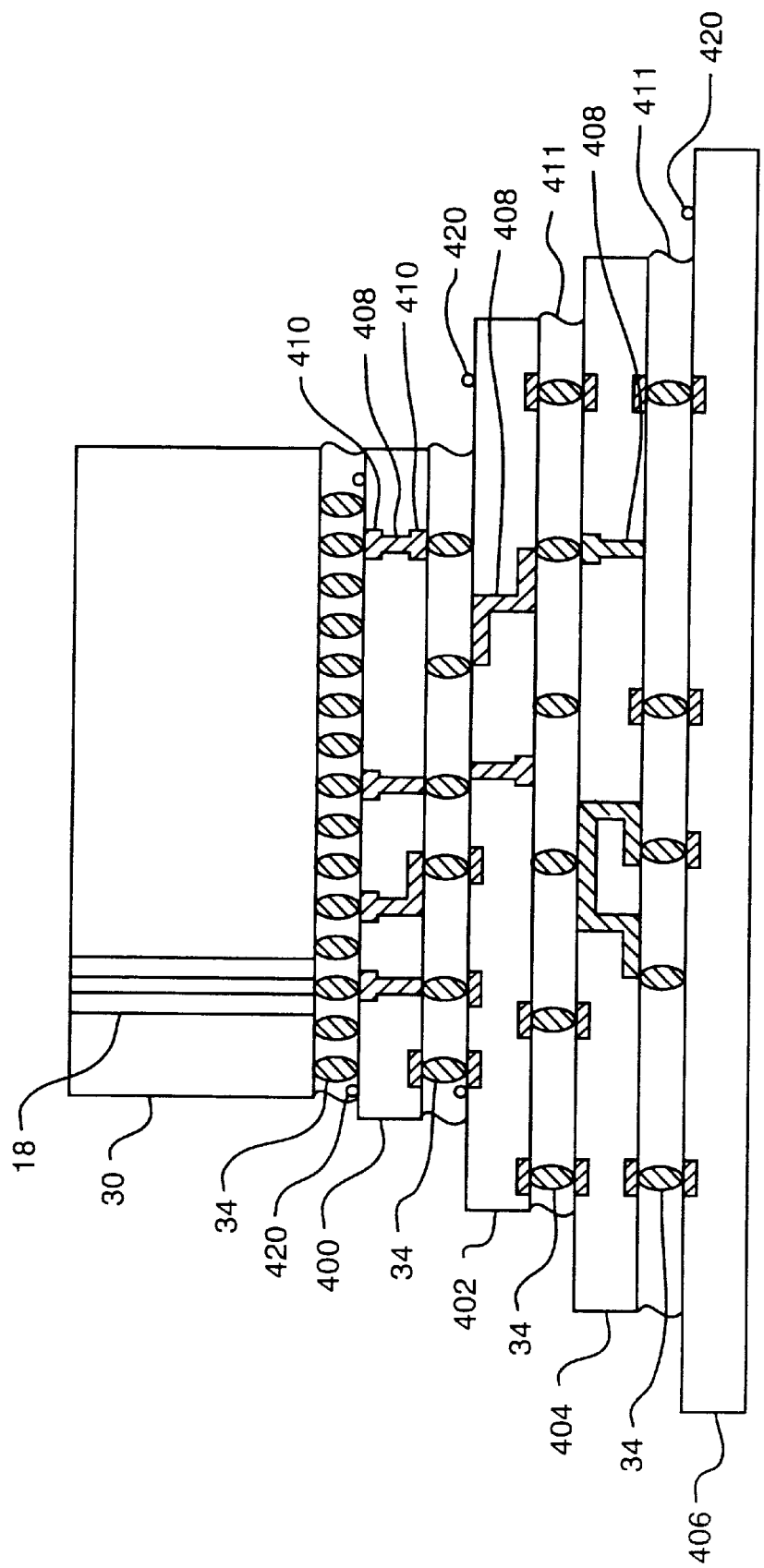
FIG. 1 is a cross section view of a representative embodiment of the invention, illustrating a multi-layer device with vias in the substrates by which inter-layer connections are accomplished.

DESCRIPTION OF THE PREFERRED EMBODIMENTS:

The invention is susceptible of many embodiments. FIG. 1 is a cross-sectional drawing of one exemplary preferred embodiment. There are four integrated circuits (ICs) and/or substrates 400, 402, 404 and 406, respectively, electrically connected to each other and to an ultrasound array 30 using:
- a. Electrically conductive micro-bumps 34 which may be of solder or an equivalent electrically conducting material with diameters on the order of 10 to 40 micrometers.
- b. One or more electrically conducting vias 408 passing through any of substrates 400–406;
- c. Electrically conducting interconnect pads 410 on the top and/or bottom sides of substrates 400–406.

Substrates 400–406 may also be mechanically connected with adhesive 412 or may simply rely on the mechanical integrity of the electrically conducting micro-bumps 34.

Figure 2:
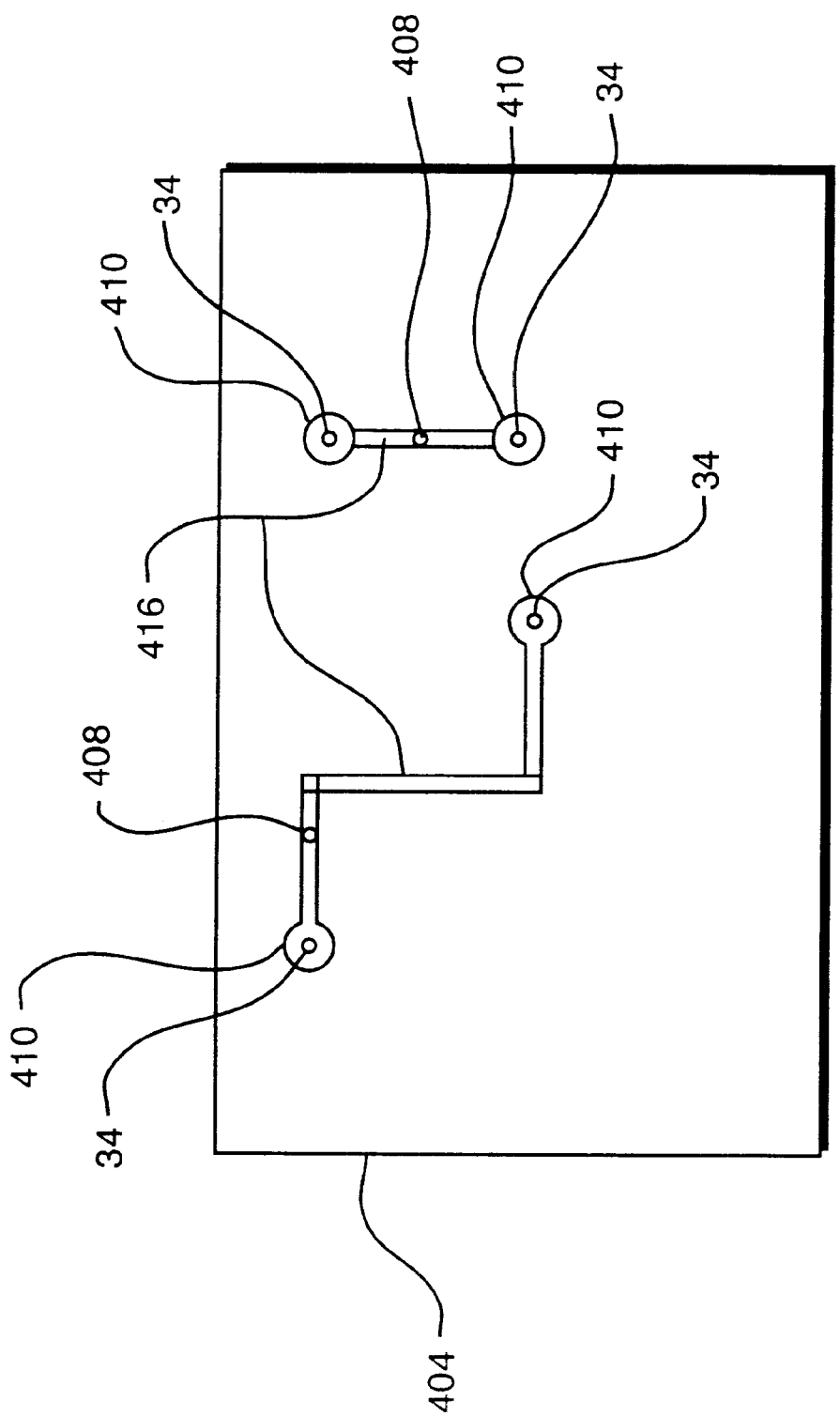
FIG. 2 is a top view of a substrate or layer of the FIG. 1 device, showing interconnecting metallization, connecting pads and vias.

FIG. 2, which is a view of the top of substrate 404, illustrates the position of vias 408 that interconnect electrically, conducting wiring 416, and associated electrically conducting pads 412. Interconnections are shown simply in FIG. 2, but they may be composed of any number of wires, vias, pads and interconnections similar to a traditional printed circuit board.

Figure 3:
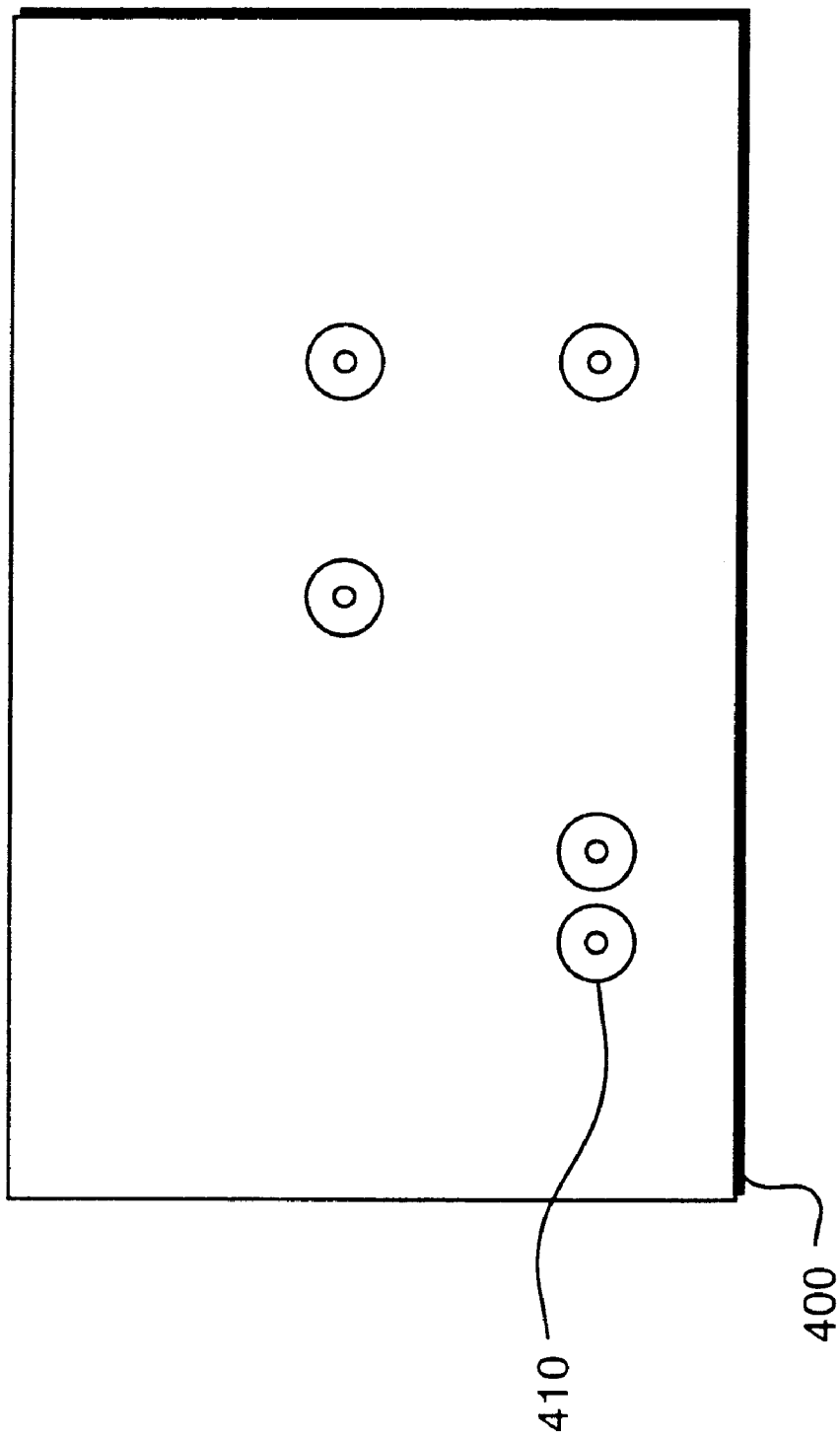
FIG. 3 is an underside view of the substrate or layer of FIG. 2, showing the underside pads that terminate the vias.
Figure 4B:
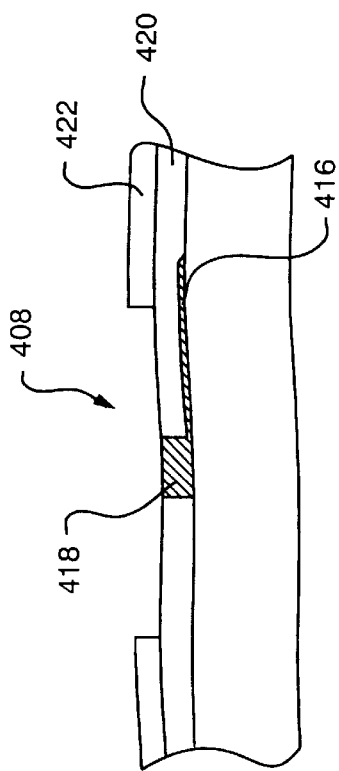
FIGS. 4A–4D are a partial perspective view and detailed cross section views of a solder bump location on a layer of the invention.
Figure 4C:
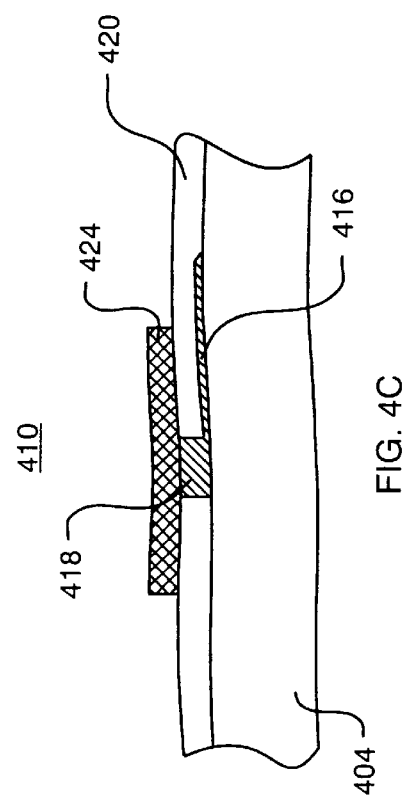
Figure 4A:
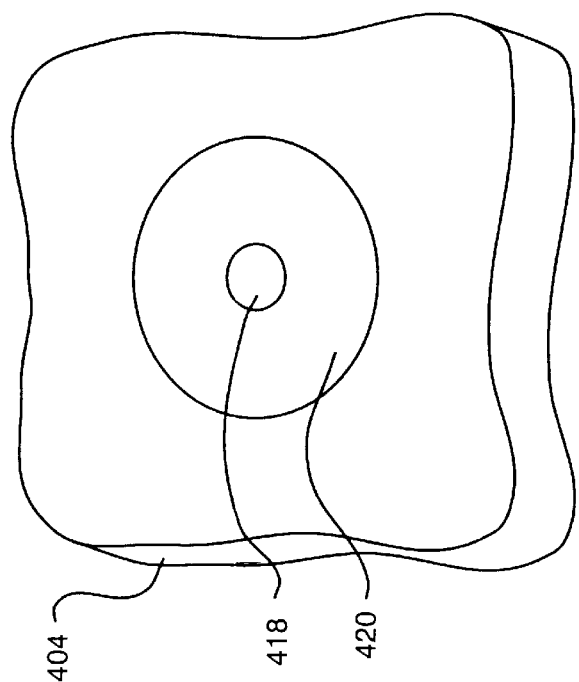
Figure 4D:
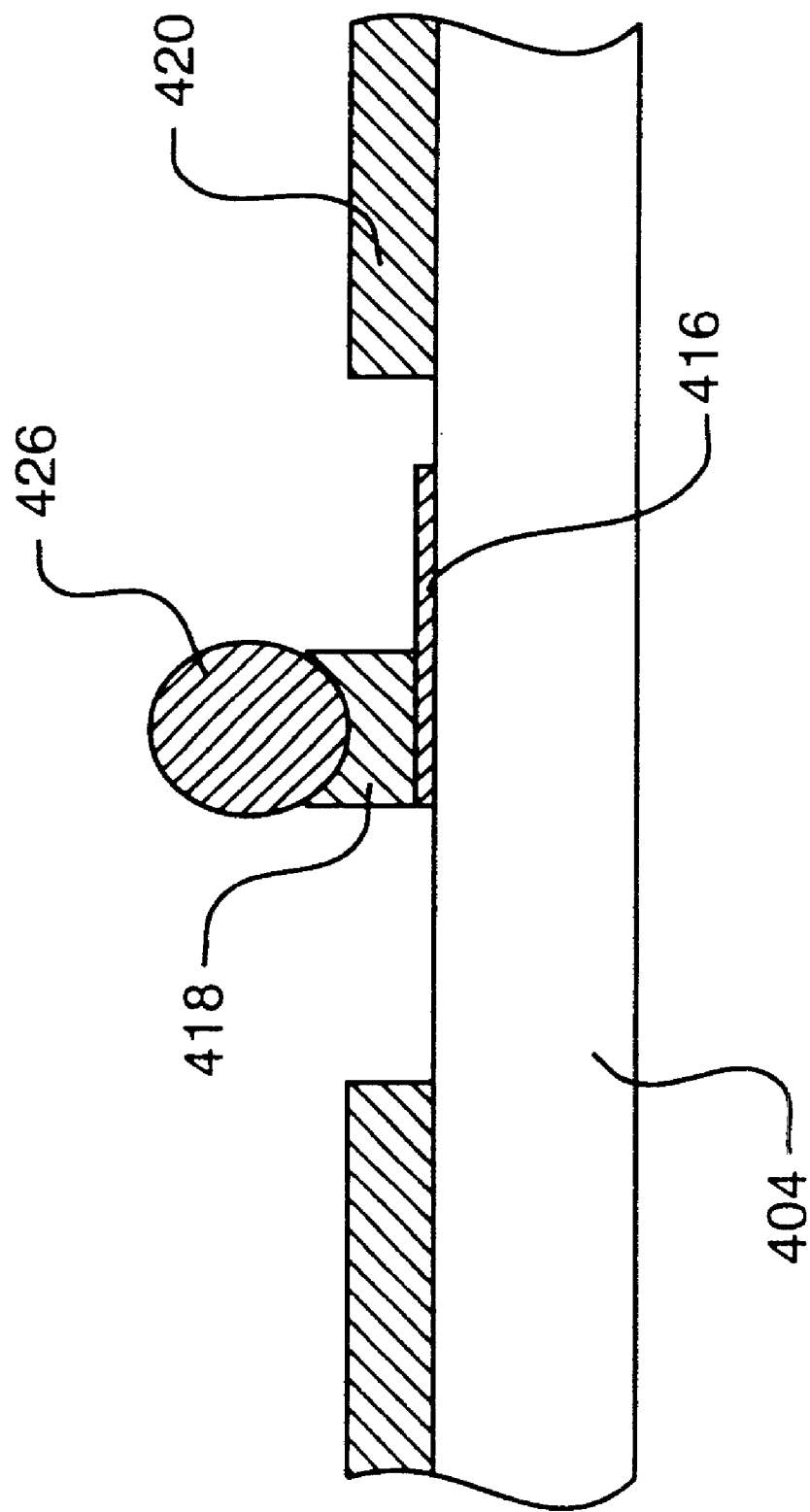

FIG. 3 is a view of the underside of substrate 400 showing interconnecting pads 408 properly positioned so that the interconnections may be made with electrically conducting micro-bumps 34. Complimentary electrically conducting pads 408 are constructed on IC 400.

Electrically conducting micro-bumps 34 are constructed using one of several well-known technologies. For example, in one preferred embodiment, the micro-bumps are composed of a solder such as a lead/tin alloy or an indium/tin alloy. In another embodiment, the micro-bumps are composed of a conductive epoxy. A third embodiment uses pure indium.

Deposition of solder requires use of established plasma or vapor deposition processes, which maintain or achieve a controlled stoichiometry of the alloy such that a known melting temperature is achieved. Fabrication of the micro-solder bumps also requires use of well known photolithographic masking and lift-off processes with dimensions appropriate for the feature size of the integrated circuits. An alternate fabrication method uses an aperture mask and vapor deposition or silk screening technology.

For example, FIGS. 4A–4D shows a typical photolithography "lift-off process" for formation of the solder bump. Substrate 404 has a deposited metalization layer 416 and a conducting pad 408. This pad consists of an "under-bump" metalization 418, which may be several different metal layers and may be different from the conducting layer 416. The under-bump metal layers are selected to provide good adhesion of the deposited solder to the conducting layer 416.

On top of layer 416 is a "solder mask" layer 420 consisting of a polymer or other material that is not wetted by the solder and therefore provides little or no adhesion. Finally, on top of the solder mask is a photoresist layer 422 of larger diameter than the solder mask.

Following deposition of solder and lift-off of the photoresist layer, a cylinder of solder 424 remains over the solder mask and which is well attached to under-bump metal pad 418. The substrate temperature is raised above melting point of the solder. Surface tension causes the molten solder to form a hemispherical shape 426. The bump height will be determined by the contact area to the under-bump metal and the volume of the solder deposited. Solder mask 420 may then be stripped away as required.

To complete the interconnection process, substrates 400–404 are mechanically aligned to bring the correct microbumps and pads into x-y registration and are pressed together.

In a preferred embodiment, the solder bumps are reflowed through application of heat, completing the electrical and mechanical interconnection. To insure proper reflow, any oxide layers that may have formed during processing must either be removed or disrupted in a flux process. Pure solder must be in contact with pure solder on the opposing substrate or a "cold-solder" joint will occur and there will be no electrical continuity. Fluxing may be accomplished using a various pastes and fluids. In the very small gap left between the parts a reducing atmosphere, containing gaseous oxygen or fluorine is the preferred method. Such methods are well known in the "flip-chip" electronics fabrication art.

In an alternate embodiment with pure indium, pressing the parts together is enough to "cold-weld" them and establish electrical continuity.

In another embodiment, two or more integrated circuits are connected together in the same manner. Each integrated circuit may use a different semiconductor technology. For example, it may be desirable to use a DMOS high voltage process on a Silicon-On-Insulator for the IC of substrate 400 and a very high density, but a more conventional CMOS process for the IC of substrate 402.

Finally, the entire structure is bump bonded to an ultrasound array using these techniques, to form an integrated matrix array.

Vias 408 of FIG. 1 are constructed by well-known substrate "drilling" techniques such as reactive ion etching together with plating of the resulting through-hole. The plating from the through hole is electrically connected to electrical connection pads on the backside of the substrate. Thus, a complete electrical circuit is established between substrate 400 and the connection pads 408. Other methods of creating a through-hole such as mechanical drilling, or laser drilling are frequently used in the semiconductor fabrication and circuit board fabrication art.

Vias in the semiconductor may be fabricated in a similar fashion. Establishing the electrical connection is more difficult due to the stray capacitance between any plating or grown polycrystalline silicon and the bulk semiconductor material. In this case, it is possible to fabricate a diode layer between the conductor and the bulk material. By biasing this diode region with a voltage, the layer may be depleted of carriers, substantially reducing the stray capacitance.

In FIG. 1, the cross-section view of a multi-layer acoustical transducer device shows the substrates with a different dimension along at least one side. This allows wire bonding 420 from pads on each substrate to facilitate interconnection to a package for testing and/or wire bonding.

In FIG. 1, several substrates are layered together using micro-solder bumps. This may be facilitated by using solders of varying melting temperatures for each interconnection layer. For example, substrate 400 is first interconnected to 404 by bumps 424 whose melting point is $t_1$. Substrate 404 is then connected to substrate 406 in a similar manner with a solder whose melting temperature is less than $t_1$. Melting temperature $t_2$ is chosen so that the micro-solder bumps in the second step do not reflow or soften. The mechanical integrity of the initial two-layer structure is thus preserved.

This type of multilayer structure with varying solder melting temperatures may be extended indefinitely by choosing appropriate solder alloys. A major advantage of this embodiment is the ability to test these structures as they are being stacked up, since the addition of the next layer does not melt the solder in the previous layer.

In particular, the technique of multiple IC layers can be exploited in an acoustical array assembly to isolate transmit and receiving circuitry for improved performance, as well as for higher density packaging, mixing of alternate IC fabrication techniques, and other related advantages. This is significant, as the transmit circuitry of an ultrasound device has high voltage and high power requirements that are much greater than the voltages and power requirements for the receiving circuitry.

Figure 5:
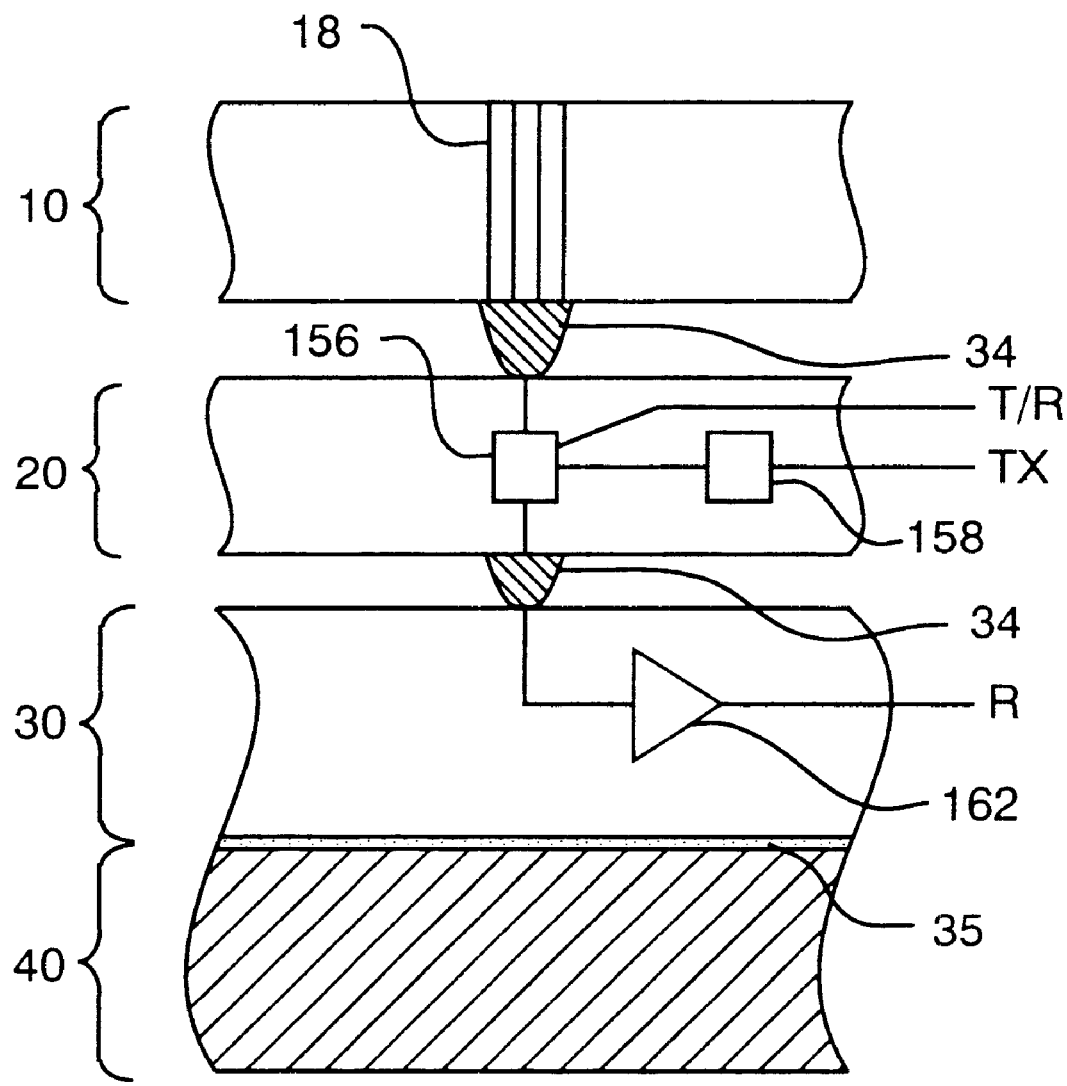
FIG. 5 is a diagrammatic cross section view of a multi-layer acoustical transducer array IC with two layers of IC and a backing.

In FIG. 5, there is shown a particularly simple and attractive first embodiment of the invention whereby transducer element 18 in layer 10 is switched between transmit and receive modes by integrated circuit layer 20. Layer 20 is comprised of high voltage circuitry including Transmit/Receive switch 156 and transmitter 158 and associated control lines. Integrated circuit layer 30 is a low voltage integrated circuit comprised of amplifier 162 and signal output line. Not shown, for clarity in this diagrammatic representation, are other integrated circuit wiring elements such as power supplies and grounds well known to those in the semiconductor design art. The high voltage integrated circuit layer is attached to an element 18 of ultrasonic transducer 10 by micro-solder bumps 34. Integrated circuit layer 30 is attached to acoustically absorbing backing 40 by adhesive layer 35 which may be fabricated so as to match the acoustical impedance of layer 30 to that of layer 40, following principle well known to those practiced in the ultrasound transducer art.

Figure 6:
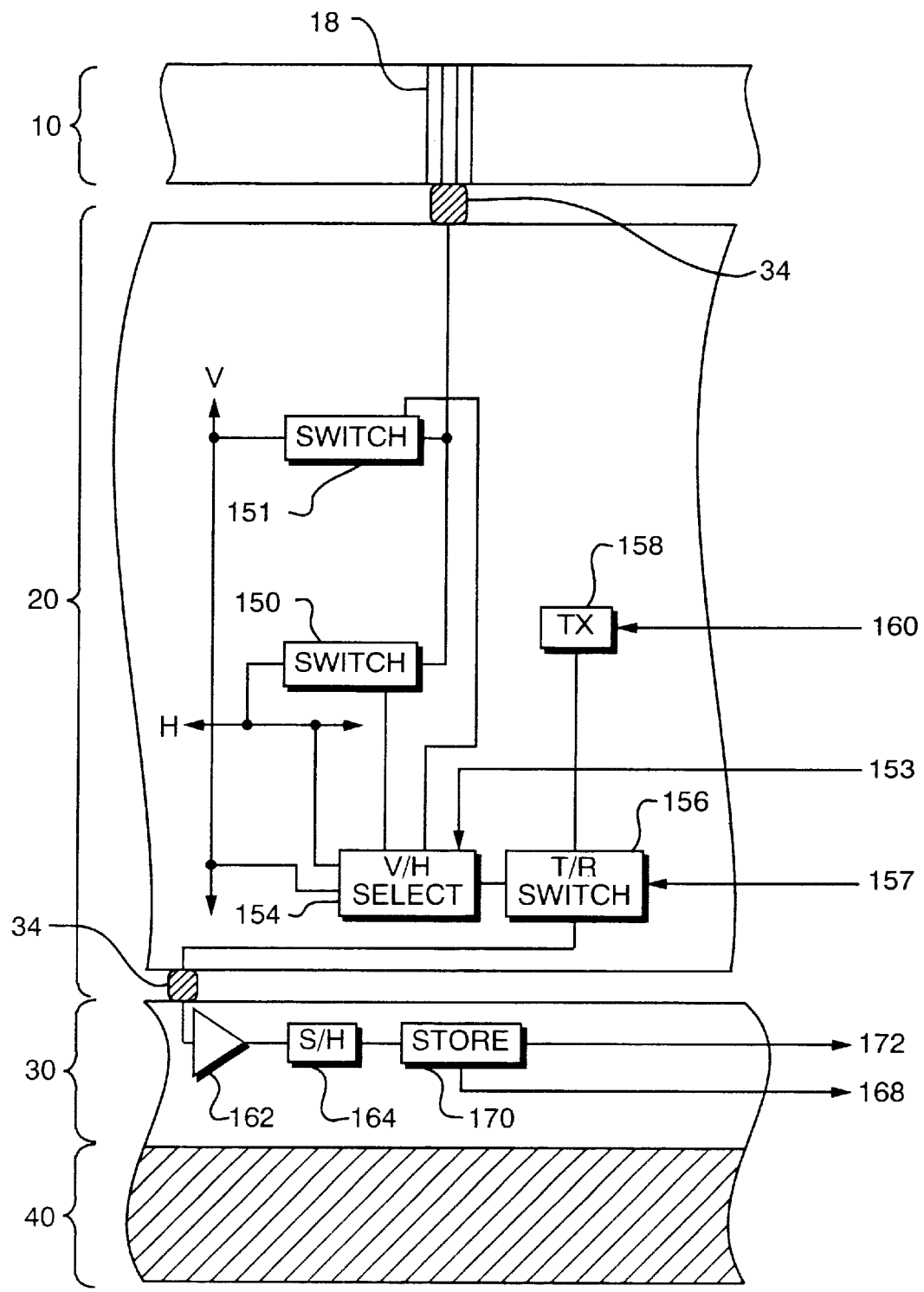
FIG. 6 is a diagrammatic cross section view of a multi-layer transducer array IC similar to FIG. 5, but with more complex circuitry distributed across two layers.

In FIG. 6, there is shown a similar multi-layered, functional equivalent of the integrated circuitry supporting a small tile or group of transducers within a larger, two dimensional acoustical transducer array, where there is a capability for selecting between groups of vertically and horizontally arranged transducers within the same tile, as described in the parent applications. In FIG. 6, an exemplary transducer array element 18 in array substrate 10 is operable through either of switches 150 and 151, depending whether the host controller signal line 153 has selected vertical or horizontal mode operation at that moment, via the adjacent vertical/horizontal mode selector switch 154. Connected to the mode selector switch 154 is the transmit/receive switch 156 for switching the selected transducers, e.g. element 18, via host controller signal line 157, between transmit circuitry 158 and receiving circuitry consisting here of preamplifier 162, sample and hold circuit 164, and analog storage circuit 170. When element 18 is selected and switched for transmit, an output signal 160 is delivered from the host controller via transmit line 160. When element 18 is selected and switched for receiving, its reflected signal output is sent back to the host controller via signal line 172.

Although this functionality can be accomplished in a single layer IC substrate, in this preferred embodiment of the invention, the receiving circuitry is resident in second IC substrate 30. Second IC substrate 30 is bump bonded to the first IC substrate 20 for electrical connections to the transmit/receive switch 156, and for electrical connections running through vias in the first IC substrate to the transducer array, which in this embodiment is flip chip mounted and bump bonded to the top side of first IC substrate 20. Layer 40 of FIG. 6, is an acoustical backing layer attached to layer 30 with a suitable adhesive such as epoxy.

Of course, the division of the integrated circuitry functionality can be expanded or divided between more than two IC substrate layers if useful, as by the addition of intermediate IC layers, and be based on other or more than just transmit and receive functions, such as the vertical/horizontal mode control function by which the two dimensional array is configured and controlled from the host controller. Other variations are within the scope of the invention, such as the mixing of IC fabrication techniques where one layer of circuit functionality is fabricated by one method, and another layer and circuit functionality is fabricated by another method.

Figure 7:
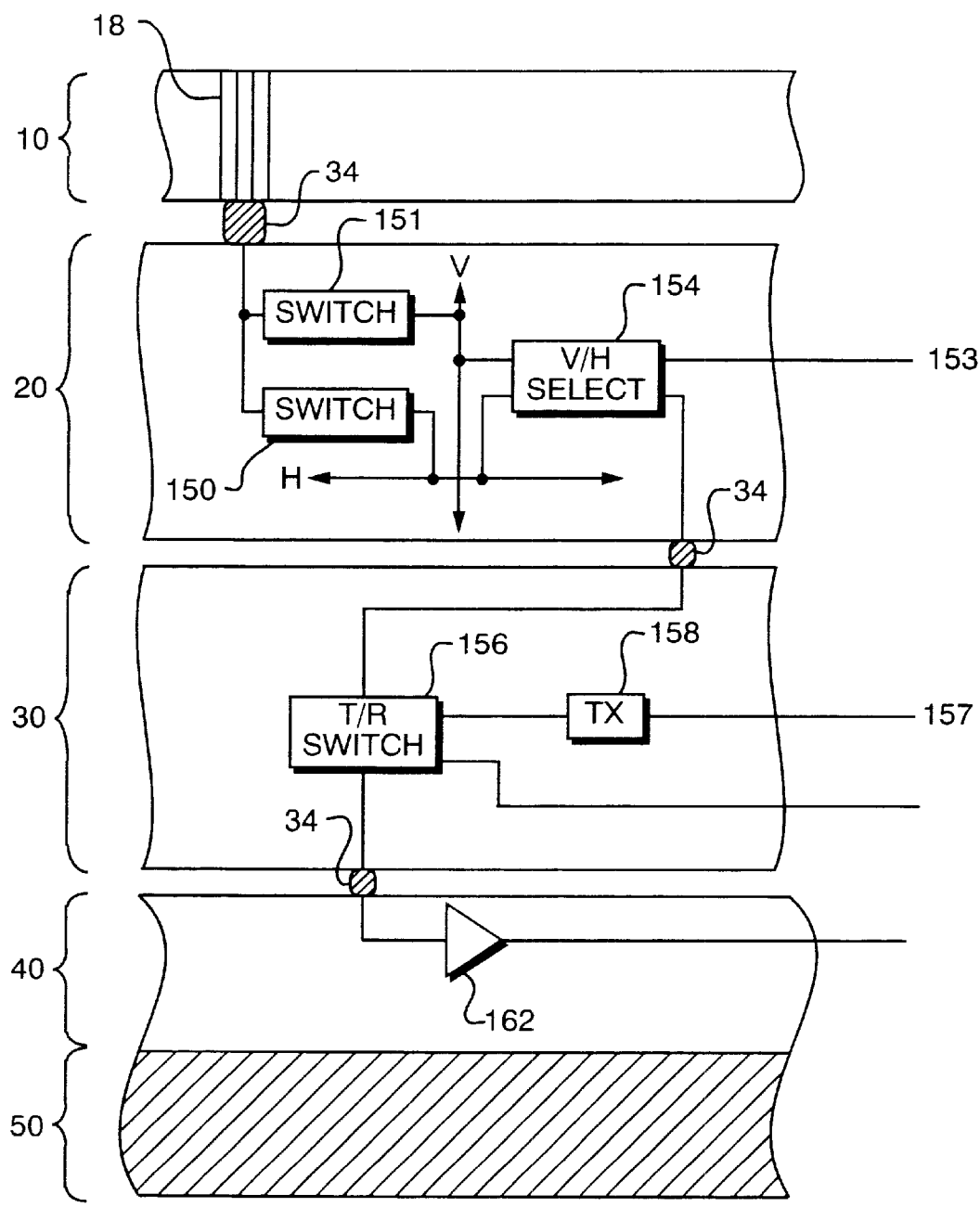
FIG. 7 is a diagrammatic cross section view of a multi-layer transducer array IC similar to FIG. 5 but with circuit elements distributed over three layers.
Figure 8:
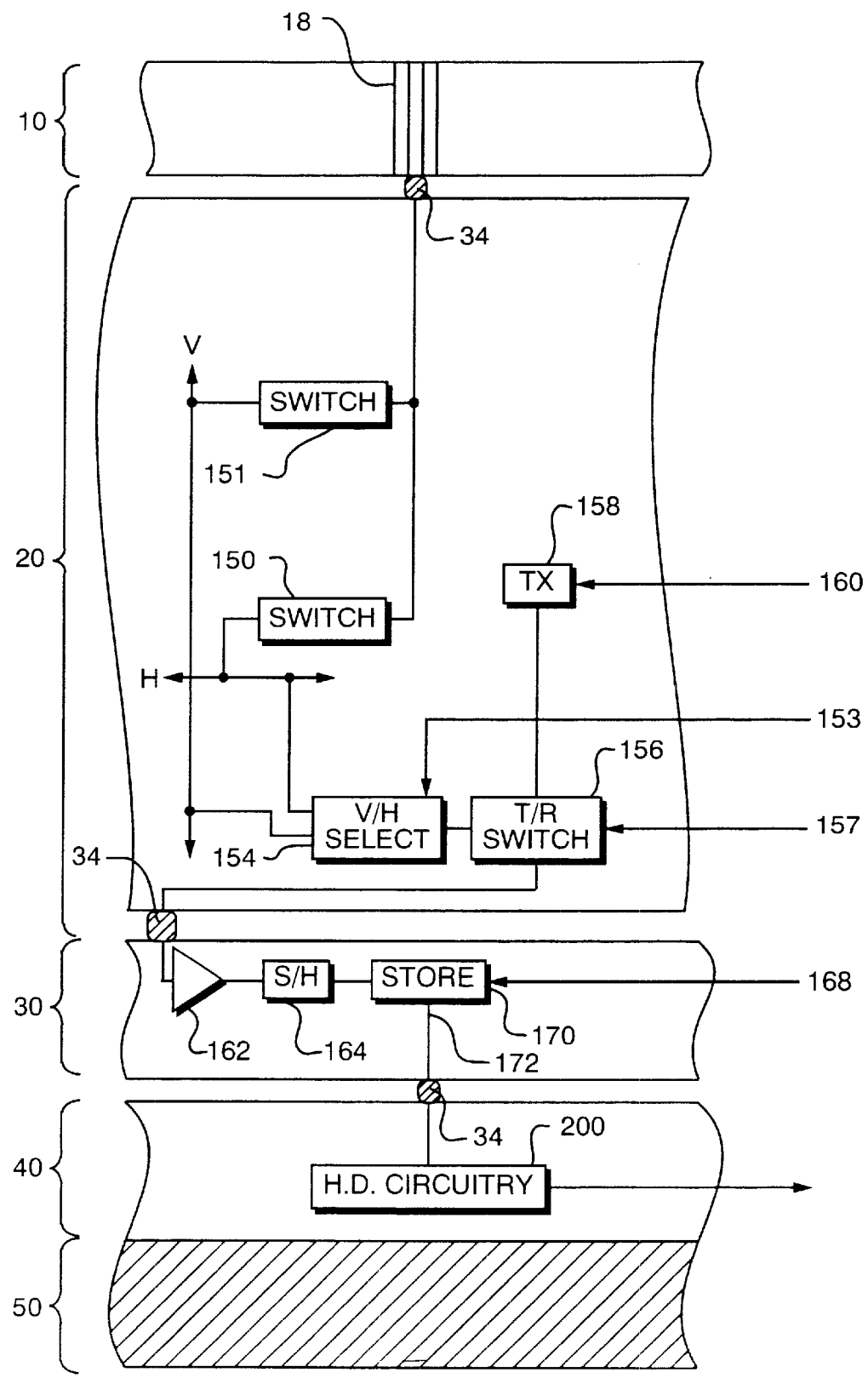
FIG. 8 is a diagrammatic cross section view of a multi-layer transducer array IC similar to FIG. 5 but with an added layer of associated high density circuitry.
Figure 9:
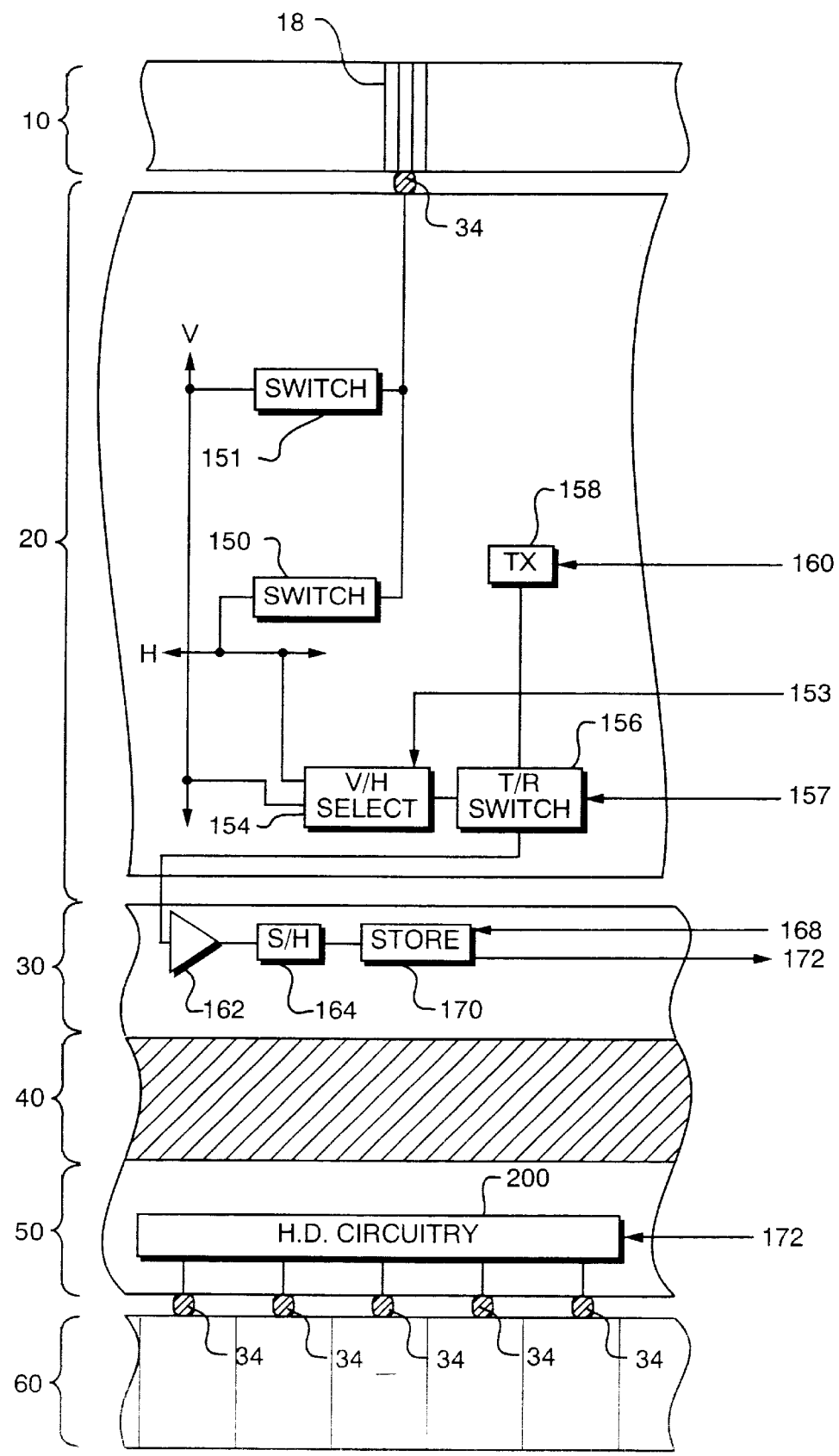
FIG. 9 is a diagrammatic cross section view of a multi-layer transducer array IC similar to FIG. 7 but with a further layer consisting of a planar display of the processed image data from the transducer array.

For example, FIGS. 8 & 9 illustrate variations on FIG. 5, where the circuit elements of the same reference numbers are variously redistributed in the respective layers. In FIG. 7, the vertical/horizontal switching circuitry is in layer 20. The transmit/receive switching function and transmit circuitry is in layer 30. The receiving circuitry is in layer 40, and layer 50 is the acoustical backing.

In FIG. 8, additional high density circuitry 200 such as data storage, that is associated with the operation of the transducer array is in layer 40, connected to layer 30 by the means described, with edge connections as required. Acoustical backing layer 50 is adhered to layer 40.

In FIG. 9, there is illustrated the further incorporation into the device of FIG. 5, a layer 50 of associated high density circuitry 200 connected by edge connection lines 172 and others as required, which is bump bonded to a layer 60 planar display array for displaying the processed image data of transducer array layer 10 as processed by the intervening layers 20–50. The displayed image may be directly viewed in some embodiments, or recorded or relayed for remote viewing.

Other and various embodiments are within the scope of the invention. For example, there is a multilayer acoustical transducer array assembly for an ultrasound system consisting of a multi-element acoustical transducer array with a front side for emitting and receiving acoustical energy, and a backside and backside pattern of electrical contacts. It has a first substrate with associated electronic circuitry for operating the array, with a first side with matching electrical contacts for contacting the backside of the transducer array and a second side with second side electrical circuit contacts. The transducer array is aligned with the first substrate, and the electrical contacts of the transducer array are electrically bonded to respective electrical contacts on the first side of the first substrate.

There is included a final substrate with additional associated electronic circuitry for operating the array, where the final substrate has at least a first side with matching electrical contacts. There may be intermediate substrates similarly constructed. The substrates are configured as successive layers from the first substrate through the final substrate, with the second side electrical contacts being electrically bonded to respective matching electrical contacts on adjacent substrates. Any or all of the substrates may be semiconductor integrated circuits.

The first substrate may have at least high voltage switches for operating the multi-element acoustical transducer array as a transmitter such that acoustical energy is emitted from the front side of the array. It may have at least switching circuitry for switching the array between emitting and receiving modes of operation.

The first substrate semiconductor integrated circuit may have at least high voltage switches for operating the multi-element acoustical transducer array as a transmitter such that acoustical energy is emitted from the front side of the array, and the final substrate semiconductor integrated circuit have at least high density, low voltage electronics for operating the to receive and further process acoustical signals received by the array. The substrates may be aligned in a co-planar configuration.

There may be at least one intermediate substrate with further associated integrated circuitry for operating the array, where the intermediate substrate has a first side with matching electrical contacts and a second side with second side electrical contacts, where the intermediate substrate is disposed between the first substrate and the final substrate. The assembly may have an acoustically attenuating layer with its front side positioned adjacent or adhered to the backside of the final substrate.

Also, one or more of the substrates may have electrical paths connecting one or more parts of its electronics circuitry or electrical contacts on said first side to respective selected electrical contacts on the second side. The electrical paths may be vias extending through the substrate, where the vias consist of or are filled with electrically conductive materials, such as a metal, metal alloy or an electrically conductive polymer.

The first substrate may further include electronic circuitry for selecting between groups of transducers within the transducer array, such as was described in more detail in the parent applications which are herein incorporated by reference. The groups of transducers available for selection may consist of orthogonally oriented lines of transducers within the transducer array, or may be other fixed or configurable subsets of the available transducers.

The electrical bonding of contacts as between substrates may be composed of solder bumps. The solder bumps between the acoustical transducer array and the first substrate may be composed of a lower melting temperature material than the solder bumps between the second side of the first substrate and the first side electrical contacts of the next sequential or final substrate.

At least one substrate, likely an intermediate or final integrated circuit substrate, has image processing capability relating to the presentation of an ultrasound image received by the array on a suitable visual display device. The assembly may include a display device such as a planar display array, electrically connected to at least one of the substrates. The planar display may be attached to the backside of the acoustically attenuating layer, configured for viewing by an operator or attendant during or coincidental to the operation of the array.

The electronic circuitry of the first substrate may have at least circuitry for switching the transducer array or elements of the array between emitting and receiving modes of operation. The electronic circuitry in the final substrate may have at least receiving circuitry for receiving signals from the array.

As another example, these capabilities may be appear in combinations of the above cited features, as are claimed below, where the substrates are aligned in a parallel or coplanar configuration. The solder bumps bonding the backside pattern of the multi-element transducer array to the first side contacts of the first substrate may be composed of a metal alloy with melting temperature $T1$, and the solder bumps bonding the second side pattern of the first substrate to the first side contacts of the first intermediate substrate may be composed of a metal alloy with melting temperature $T2$, and so on, with the solder bumps bonding the second side pattern of the last intermediate substrate to the first side contacts of the final substrate being composed of a metal alloy with melting temperature $T3$.

Where $T1$ is less than $T2$, and $T2$ is less than $T3$, and intermediate layers follow the same rule, the successive layers of gradually lower melting solder temperatures provides for progressive assembly with intermediate level testing prior to attachment of the array. Alternatively, this temperature selection and assembly progression can begin at any desired intermediate substrate, and progress both ways from high to lower temperatures towards final attachment of the array on one side and the last substrate or visual display on the other side of the full assembly.

Various embodiments may employ electrical bonding materials including any of a metal, metal alloy or an electrically conductive polymer.

The associated integrated circuitry in a first or intermediate integrated circuit substrate may have at least switching circuitry for switching the array between transmitting and receiving modes of operation. The associated integrated circuitry in the final integrated circuit substrate may have at least receiving circuitry for receiving signals from the array.

Yet other embodiments may have substrates configured in other than parallel planes, including convex, concave or co-planar configurations. Acoustical imaging probes use planar, convex or concave transducer arrays, depending on the application and the complexity of the system electronics.

For example, planar phased arrays are used in cardiology where a minimum contact area on the skin is required. In this application, the sound beam must be introduced into the body between the ribs, which form a barrier and a reverberation source for the sound beam and must be avoided. To create a wide angle sector scan, such a probe requires an increased number of channels and increased electronics complexity compared to a convex or concave array.

The convex array is the most common array format and is especially useful in the abdomen. The curved surface, in contact with the skin, provides the sector scanning function with simplified electronics. Phased array electronics may not be required at all, although most systems have at least a limited phased array capability for electronic focusing.

The concave array uses similar simplified electronics as the convex array to produce a small footprint for sound to enter the body. It is larger than either the planar or convex array and is not in common use today.

As an additional example, the invention is inclusive of a method for making a multilayer acoustical transducer array assembly including the preliminary step of providing an acoustical transducer array with a backside pattern of electrical contacts, a first integrated circuit substrate with a first side with matching electrical contacts to the backside pattern of electrical contacts of the array and a second side with a second side pattern of electrical contacts, where the first integrated circuit substrate has associated integrated electronic circuitry for supporting the operation of the array and electrical paths connecting selected matching electrical contacts on its first side to respective selected electrical contacts on its second side, and the electrical paths are vias extending through the substrate and consist of electrically conductive materials. There is included a second integrated circuit substrate having at least a first side of matching electrical contacts and integrated electronic circuitry for supporting the operation of said array.

The next step is to electrically bond the matching electrical contacts on the first side of the second integrated circuit substrate to the electrical contacts on the second side of the first integrated circuit substrate at a first temperature. This is followed by the step of electrically bonding the matching electrical contacts on the first side of the first integrated circuit substrate to the electrical contacts of the array at a second temperature, where the second temperature is lower than the first temperature. There may be interposed a step for testing at least selected electrical functions of the second integrated circuit substrate at least in part through access to the electrical contacts on the first side of the first integrated circuit substrate, prior to bonding the array to the first substrate. The method extends to adding more substrates and more intermediate testing, prior to bonding the array to the first substrate and/or a visual display to the other side of the assembly.

These embodiments are exemplary. The integration of full data processing and image display capability with a full two dimension acoustical transducer array into a single IC device may require additional layers of circuitry, depending on size and complexity. Other and various embodiments within the scope of the invention will be readily apparent to those skilled in the art, from the specification, figures and the claims that follow.

What is claimed is:

1. A multilayer acoustical transducer array assembly for an ultrasound system comprising a multi-element acoustical transducer array with a front side for emitting and receiving acoustical energy, a backside and a backside pattern of electrical contacts, a first substrate with associated electronic circuitry for operating the array, said first substrate having a first side with matching electrical contacts for contacting said backside of said transducer array and a second side with second side electrical circuit contacts, said transducer array being aligned with said first substrate, said electrical contacts of said transducer array being electrically bonded to respective said electrical contacts on said first side of said first substrate, and a final substrate with additional associated electronic circuitry for operating the array, said final substrate having at least a first side with matching electrical contacts, said substrates being configured as successive layers from said first substrate to said final substrate, said second side electrical contacts being electrically bonded to respective said matching electrical contacts on adjacent said substrates.

2. A multilayer acoustical transducer array assembly according to claim 1, wherein said first substrate is a semiconductor integrated circuit.

3. A multilayer acoustical transducer array assembly according to claim 2, said first semiconductor integrated circuit comprising at least high voltage switches for operating said multi-element acoustical transducer array as a transmitter such that acoustical energy is emitted from said front side of said acoustical transducer array.

4. A multilayer acoustical transducer array assembly according to claim 2, said semiconductor integrated circuit comprising at least switching circuitry for switching said array between emitting and receiving modes of operation.

5. A multilayer acoustical transducer array assembly according to claim 1, wherein said first and said final substrates are semiconductor integrated circuits.

6. A multilayer acoustical transducer array assembly according to claim 5, wherein said first semiconductor integrated circuit is comprised of at least high voltage switches for operating said multi-element acoustical transducer array as a transmitter such that acoustical energy is emitted from said front side of said acoustical transducer array and said final semiconductor integrated circuit is comprised of at least high density, low voltage electronics for operating said multi-element acoustical transducer array to receive and further process acoustical signals received by said acoustical transducer array.

7. A multilayer acoustical transducer array assembly according to claim 1, wherein said multi-element acoustical transducer array, said first substrate and said final substrate are aligned in a co-planar configuration.

8. A multilayer acoustical transducer array assembly according to claim 1, further comprising at least one intermediate substrate with further associated integrated circuitry for operating the array, said intermediate substrate having a first side with matching electrical contacts and a second side with second side electrical contacts, said intermediate substrate disposed between said first substrate and said final substrate.

9. A multilayer acoustical transducer array assembly according to claim 8, wherein at least one said intermediate integrated circuit substrate has image processing capability.

10. A multilayer acoustical transducer array assembly according to claim 1, further comprising an acoustically attenuating layer with a backside, and a front side adhered to said backside of said final substrate.

11. A multi-layer acoustical transducer array assembly according to claim 10, further comprising a planar display array electrically connected to at least one of said substrates.

12. A multi-layer acoustical transducer array assembly according to claim 11, said planar display attached to the backside of said acoustically attenuating layer.

13. A multilayer acoustical transducer array assembly according to claim 1, wherein at least one said substrate has electrical paths connecting one or more parts of said electronics circuitry on said first side to respective selected electrical contacts on said second side.

14. A multilayer acoustical array assembly according to claim 13, said electrical paths comprising vias extending through said substrate, said vias comprising electrically conductive materials.

15. A multilayer acoustical array assembly according to claim 1, said first substrate further comprising electronic circuitry for selecting between groups of transducers within said transducer array.

16. A multilayer acoustical transducer array assembly according to claim 15, said groups of transducers comprising orthogonally oriented lines of transducers within said transducer array.

17. A multilayer acoustical transducer array assembly according to claim 1, said electrical bonding being composed of solder bumps.

18. A multilayer acoustical transducer array assembly according to claim 17, wherein said solder bumps between said acoustical transducer array and said first substrate are composed of a lower melting temperature material than said solder bumps between said second side of said first substrate and said first side electrical contacts of said final substrate.

19. A multilayer acoustical transducer array assembly according to claim 1, said electronic circuitry of said first substrate comprising at least circuitry for switching said multi-element transducer array between emitting and receiving modes of operation, said electronic circuitry in said final substrate comprising at least receiving circuitry for receiving signals from said array.

20. A multilayer acoustical transducer array assembly for an ultrasound imaging system comprising a multi-element acoustical transducer array with a front side for emitting and receiving acoustical signals and a backside and backside pattern of electrical contacts, a first substrate with electronic circuitry for operating the array, said first substrate having a first side with matching electrical contacts for contacting said transducer array for operation and a second side with second side electrical circuit contacts, said transducer array being aligned in a co-planar configuration with said first substrate, said electrical contacts of said transducer array being electrically bonded to respective said electrical contacts on said first side of said first substrate, and at least one intermediate substrate with further associated electronic circuitry for operating the array, said intermediate integrated circuit substrate having a first side with matching electrical contacts and a second side with second side electrical contacts, a final integrated circuit substrate with additional said associated electronic circuitry for operating the array, said final substrate having a first side with matching electrical contacts and a second side, all said substrates being aligned in a co-planar configuration, said second side electrical contacts of each said substrate being electrically bonded to respective said matching electrical contacts on each adjacent said substrate, and an acoustical backing layer adhered to said second side of said final substrate, said first substrate having electrical paths connecting at least selected said electrical contacts on said first side to respective selected electrical contacts on said second side, said electrical paths comprising vias extending through said substrate, said vias comprising electrically conductive materials.

21. A multilayer acoustical array assembly according to claim 20, said first integrated circuit substrate further comprising circuitry for selecting between groups of transducers within said transducer array.

22. A multilayer acoustical transducer array assembly according to claim 21, said groups of transducers comprising orthogonally oriented lines of transducers within said transducer array.

23. A multilayer acoustical transducer array assembly according to claim 20, said electrical bonding being composed of solder bumps.

24. A multilayer acoustical transducer array assembly according to claim 23, said solder bumps bonding said backside pattern of said multi-element transducer array to said first side contacts of said first substrate being composed of a metal alloy with melting temperature T1, and said solder bumps bonding said second side pattern of said first substrate to said first side contacts of said intermediate substrate being composed of a metal alloy with melting temperature T2, and said solder bumps bonding said second side pattern of said intermediate substrate to said first side contacts of said final substrate being composed of a metal alloy with melting temperature T3, where T1 is less than T2, and T2 is less than T3.

25. A multilayer acoustical transducer array assembly according to claim 20, said electrical bonding being composed of an electrically conductive polymer.

26. A multilayer acoustical transducer array assembly according to claim 20, said associated integrated circuitry in said intermediate integrated circuit substrate comprising at least switching circuitry for switching said array between transmitting and receiving modes of operation.

27. A multilayer acoustical transducer array assembly according to claim 20, said associated integrated circuitry in said final integrated circuit substrate comprising at least receiving circuitry for receiving signals from said array.

28. A multilayer acoustical transducer array assembly comprising a multi-element acoustical transducer array with a front side for transmitting and receiving acoustical energy, a backside and backside pattern of electrical contacts, a first integrated circuit substrate with associated electronic circuitry for operating the array, said first substrate having a first side with matching electrical connections to said transducer array for conducting electrical signals between said transducer array and said first integrated circuit and a second side with second side electrical circuit contacts, a final integrated circuit substrate with additional associated electronic circuitry for operating the array, said final integrated circuit substrate having at least a first side with matching electrical contacts, said substrates being configured as successive layers from said first integrated circuit substrate to said final integrated circuit substrate, said second side electrical contacts being electrically bonded to respective said matching electrical contacts on adjacent said substrates, with said acoustical transducer array and all said substrates being aligned in a convex, concave or co-planar configuration, said second side electrical contacts of each said integrated circuit substrate being electrically bonded to respective said matching electrical contacts on each adjacent said integrated circuit substrate with solder bumps, and an acoustical backing layer adhered to said second side of said final integrated circuit substrate, said first integrated circuit substrate having electrical paths connecting at least selected said electrical contacts on said first side to respective selected electrical contacts on said second side, said electrical paths comprising vias extending through said integrated circuit substrate, said vias comprising electrically conductive materials, said associated integrated circuitry in said first integrated circuit substrate comprising at least switching circuitry for switching said array between transmitting and receiving modes of operation, said associated integrated circuitry in said final integrated circuit substrate comprising at least receiving circuitry for receiving signals from said array.

29. A multilayer acoustical transducer array assembly according to claim 28, said solder bumps between said final integrated circuit substrate and said first integrated circuit substrate being composed of a material with a higher reflow melting temperature than said solder bumps between said first integrated circuit substrate and said acoustical transducer array.

30. A method for making a multilayer acoustical transducer array assembly comprising the steps:

providing an acoustical transducer array with a backside pattern of electrical contacts, a first integrated circuit substrate with a first side with matching electrical contacts to said backside pattern of electrical contacts of said acoustical transducer array and a second side with a second side pattern of electrical contacts, said first integrated circuit substrate comprising associated integrated electronic circuitry for supporting the operation of said array and electrical paths connecting selected said matching electrical contacts on said first side thereof to respective selected electrical contacts on said second side thereof, said electrical paths comprising vias extending through said integrated circuit substrate, said vias comprising electrically conductive materials, and a second integrated circuit substrate having at least a first side of matching electrical contacts and comprising integrated electronic circuitry for supporting the operation of said array, and electrically bonding said matching electrical contacts on said first side of said second integrated circuit substrate to said electrical contacts on second side of said first integrated circuit substrate at a first temperature, and electrically bonding the matching electrical contacts on the first side of said first integrated circuit substrate to said electrical contacts of said array at a second temperature, said second temperature being lower than said first temperature.

31. A method for making a multilayer acoustical transducer array assembly according to claim 30, comprising the additional step, prior to the step of electrically bonding the matching electrical contacts on the first side of said first integrated circuit substrate to said electrical contacts of said array, of testing at least selected electrical functions of said second integrated circuit substrate at least in part through access to the electrical contacts on the first side of said first integrated circuit substrate.

32. A method for making a multilayer acoustical transducer array assembly according to claim 30, comprising the further steps:

provinding said second integrated circuit substrate with a second side with electrical contacts and electrical paths connecting selected said matching electrical contacts on said first side thereof to respective selected electrical contacts on said second side thereof, said electrical paths comprising vias extending through said integrated circuit substrate, said vias comprising electrically conductive materials, and providing a third integrated circuit substrate comprising additional integrated circuitry for supporting the operation of said array and having at least a first side of matching electrical contacts, and prior to electrically bonding said first substrate to said second substrate, electrically bonding the matching electrical contacts on the first side of said third integrated circuit substrate to the electrical contacts on said second side of said second integrated circuit substrate at a third temperature, said third temperature being higher than said second temperature.

33. A method for making a multilayer acoustical transducer array assembly according to claim 32, comprising the additional step, prior to the step of electrically bonding the matching electrical contacts on the first side of said first integrated circuit substrate to said electrical contacts of said array, of testing at least selected electrical functions of said third integrated circuit substrate at least in part through access to the electrical contacts on the first side of said second integrated circuit substrate.

\* \* \* \* \*

UNITED STATES PATENT AND TRADEMARK OFFICE
CERTIFICATE OF CORRECTION

PATENT NO. : 6,589,180 B2
DATED : July 8, 2003
INVENTOR(S) : Kenneth R. Erikson, John Marciniec and Timothy E. White It is certified that error appears in the above-identified patent and that said Letters Patent is hereby corrected as shown below:

Column 3,
Line 34, "28" should be bolded

Column 8,
Line 66, delete "412", insert -- 410 --

Column 9,
Line 4, delete "412", insert -- 410 --
Line 9,12 and 31, delete "408", insert -- 410 --

Column 10,
Line 17, delete "408", insert -- 410 --
Lines 38 and 39, delete "404", insert -- 402 --
Line 38, delete "424", insert -- 34 --
Line 39, delete "406", insert -- 404 --

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,589,180 B2
DATED : July 8, 2003
INVENTOR(S) : Kenneth R. Erikson, John Marciniec and Timothy E. White It is certified that error appears in the above-identified patent and that said Letters Patent is hereby corrected as shown below:

Column 3,
Line 34, "28" should be bolded

Column 8,
Line 66, delete "412", insert -- 411 --

Column 9,
Line 4, delete "412", insert -- 410 --
Line 9,12 and 31, delete "408", insert -- 410 --

Column 10,
Line 17, delete "408", insert -- 410 --
Lines 38 and 39, delete "404", insert -- 402 --
Line 38, delete "424", insert -- 34 --
Line 39, delete "406", insert -- 404 --

This certificate supersedes Certificate of Correction issued August 24, 2004.

Signed and Sealed this

Ninth Day of November, 2004

JON W. DUDAS
*Director of the United States Patent and Trademark Office*